United States Patent
Chung et al.

(10) Patent No.: US 8,298,131 B2
(45) Date of Patent: Oct. 30, 2012

(54) SYSTEM AND METHOD FOR RELAXATION

(75) Inventors: Joanne Wai Yee Chung, Kowloon (HK); Thomas Kwok Shing Wong, Kowloon (HK); William Chi Keung Cheung, Kowloon (HK); Benny Yat Sing Lam, Kowloon (HK); Suk Yin Chow, Kowloon (HK); Henry Chi Fuk So, Kowloon (HK)

(73) Assignee: The Hong Kong Polytechnic University, Kowloon (HK)

( * ) Notice: Subject to any disclaimer, the term of this patent is extended or adjusted under 35 U.S.C. 154(b) by 1034 days.

(21) Appl. No.: 12/263,363

(22) Filed: Oct. 31, 2008

(65) Prior Publication Data

US 2010/0113865 A1    May 6, 2010

(51) Int. Cl.
*A61M 21/00* (2006.01)
(52) U.S. Cl. ............................. 600/27; 600/26
(58) Field of Classification Search .............. 600/27, 600/26
See application file for complete search history.

(56) References Cited

U.S. PATENT DOCUMENTS

| | | | | |
|---|---|---|---|---|
| 5,267,568 A * | 12/1993 | Takara | ................ | 600/500 |
| 6,306,077 B1 * | 10/2001 | Prabhu et al. | ............. | 600/26 |
| 6,358,201 B1 * | 3/2002 | Childre et al. | ............. | 600/300 |
| 2002/0128563 A1 * | 9/2002 | Carlson et al. | ............. | 600/509 |
| 2005/0256414 A1 * | 11/2005 | Kettunen et al. | ........... | 600/509 |
| 2008/0319252 A1 * | 12/2008 | Chapman et al. | ........... | 600/27 |

* cited by examiner

*Primary Examiner* — Charles A Marmor, II
*Assistant Examiner* — Sunita Reddy
(74) *Attorney, Agent, or Firm* — Muncy, Geissler, Olds & Lowe, PLLC

(57) ABSTRACT

A system (10) for relaxation, the system (10) comprising: electrodes (15) worn by a user to measure the electrocardiogram (ECG) of the user; a processor (18) to process the ECG to remove noise and analyse the ECG signal in the time and frequency domains, and compute an index of stress (33) from the processed ECG; and a multimedia device (14) to provide real-time biofeedback by communicating the index of stress (33) to the user together with a relaxation video (31) to cause the user to relax.

8 Claims, 8 Drawing Sheets

Figure 10

| | | | | | | | | | | | |
|---|---|---|---|---|---|---|---|---|---|---|---|
| 1 | 814.404056 | 51 | 857.694341 | 101 | 845.662887 | 151 | 707.204172 | 201 | 735.889018 | 251 | 786.296881 |
| 2 | 350 | 52 | 830.612434 | 102 | 867.509593 | 152 | 709.259398 | 202 | 760.89446 | 252 | 811.327756 |
| 3 | 350 | 53 | 810.079807 | 103 | 871.320116 | 153 | 699.633485 | 203 | 778.120209 | 253 | 807.911056 |
| 4 | 350 | 54 | 806.501769 | 104 | 866.707418 | 154 | 723.91335 | 204 | 716.689969 | 254 | 817.281233 |
| 5 | 350 | 55 | 845.912848 | 105 | 845.412227 | 155 | 722.553636 | 205 | 713.234673 | 255 | 816.416961 |
| 6 | 433.302369 | 56 | 827.174325 | 106 | 833.284962 | 156 | 724.608171 | 206 | 721.820358 | 256 | 773.902741 |
| 7 | 666.330371 | 57 | 865.132425 | 107 | 795.515931 | 157 | 726.450046 | 207 | 722.89629 | 257 | 755.105263 |
| 8 | 687.374732 | 58 | 865.669755 | 108 | 802.185458 | 158 | 741.005076 | 208 | 735.46279 | 258 | 760.063035 |
| 9 | 710.084369 | 59 | 864.384074 | 109 | 836.291142 | 159 | 768.655074 | 209 | 741.531367 | 259 | 746.998183 |
| 10 | 689.890194 | 60 | 840.086401 | 110 | 866.398163 | 160 | 769.65489 | 210 | 723.575048 | 260 | 762.243963 |
| 11 | 673.977932 | 61 | 810.870106 | 111 | 863.941355 | 161 | 751.803064 | 211 | 729.505016 | 261 | 773.181638 |
| 12 | 671.636168 | 62 | 815.325453 | 112 | 853.213098 | 162 | 750.647746 | 212 | 717.652024 | 262 | 763.835887 |
| 13 | 695.918933 | 63 | 794.417286 | 113 | 821.413503 | 163 | 743.364297 | 213 | 719.987699 | 263 | 778.314076 |
| 14 | 758.431422 | 64 | 783.90834 | 114 | 807.378851 | 164 | 748.063697 | 214 | 735.649848 | 264 | 802.253872 |
| 15 | 826.358781 | 65 | 811.200892 | 115 | 816.551447 | 165 | 743.012565 | 215 | 742.166459 | 265 | 805.348117 |
| 16 | 848.346167 | 66 | 822.98379 | 116 | 826.604509 | 166 | 728.289027 | 216 | 763.545395 | 266 | 795.00911 |
| 17 | 856.531917 | 67 | 829.388816 | 117 | 829.53207 | 167 | 732.542286 | 217 | 764.014428 | 267 | 786.496312 |
| 18 | 801.402825 | 68 | 796.101625 | 118 | 860.112036 | 168 | 747.704945 | 218 | 769.761666 | 268 | 785.896531 |
| 19 | 745.933049 | 69 | 832.332539 | 119 | 840.293174 | 169 | 761.21046 | 219 | 748.585762 | 269 | 794.919231 |
| 20 | 737.821207 | 70 | 837.386247 | 120 | 836.936048 | 170 | 772.373661 | 220 | 737.717375 | 270 | 774.162174 |
| 21 | 723.611281 | 71 | 843.749808 | 121 | 776.174 | 171 | 797.982182 | 221 | 732.739375 | 271 | 766.954332 |
| 22 | 756.536585 | 72 | 831.540752 | 122 | 719.386675 | 172 | 796.022384 | 222 | 738.73121 | 272 | 774.359066 |
| 23 | 770.986918 | 73 | 792.47774 | 123 | 720.292607 | 173 | 749.168471 | 223 | 738.270091 | 273 | 753.851114 |
| 24 | 740.219703 | 74 | 808.666325 | 124 | 748.872059 | 174 | 706.461747 | 224 | 717.817937 | 274 | 747.233338 |
| 25 | 723.160994 | 75 | 814.471452 | 125 | 763.141453 | 175 | 675.236823 | 225 | 691.352077 | 275 | 719.121096 |
| 26 | 749.586445 | 76 | 851.265449 | 126 | 805.504149 | 176 | 667.731649 | 226 | 672.219648 | 276 | 688.952759 |
| 27 | 788.026005 | 77 | 822.222953 | 127 | 840.207642 | 177 | 690.998076 | 227 | 666.075802 | 277 | 682.262148 |
| 28 | 829.562776 | 78 | 861.486429 | 128 | 819.45634 | 178 | 708.219363 | 228 | 660.690386 | 278 | 750.020098 |
| 29 | 855.573427 | 79 | 848.275449 | 129 | 809.945813 | 179 | 742.848081 | 229 | 667.281346 | 279 | 772.590022 |
| 30 | 806.233567 | 80 | 824.29246 | 130 | 802.341853 | 180 | 805.397459 | 230 | 829.972265 | 280 | 763.650598 |
| 31 | 811.616796 | 81 | 763.160921 | 131 | 775.175139 | 181 | 791.011947 | 231 | 853.552842 | 281 | 773.365935 |
| 32 | 790.224996 | 82 | 705.087368 | 132 | 751.37832 | 182 | 784.926126 | 232 | 813.602607 | 282 | 761.904574 |
| 33 | 755.599896 | 83 | 723.529757 | 133 | 738.63876 | 183 | 768.98301 | 233 | 787.121684 | 283 | 750.979715 |
| 34 | 763.156285 | 84 | 760.956532 | 134 | 742.983554 | 184 | 766.919789 | 234 | 786.653641 | 284 | 735.221049 |
| 35 | 772.109223 | 85 | 791.2836 | 135 | 742.360837 | 185 | 752.39602 | 235 | 773.345991 | 285 | 721.357287 |
| 36 | 812.033289 | 86 | 854.856077 | 136 | 761.781742 | 186 | 716.46171 | 236 | 764.521267 | 286 | 733.31376 |
| 37 | 858.349076 | 87 | 838.59896 | 137 | 782.418801 | 187 | 715.300287 | 237 | 785.770559 | 287 | 753.651231 |
| 38 | 885.31277 | 88 | 820.103654 | 138 | 813.584606 | 188 | 699.369782 | 238 | 772.253208 | 288 | 795.603634 |
| 39 | 865.809114 | 89 | 812.07542 | 139 | 808.693999 | 189 | 723.866054 | 239 | 748.087673 | 289 | 825.875845 |
| 40 | 849.181782 | 90 | 781.650247 | 140 | 811.508935 | 190 | 788.692147 | 240 | 758.090359 | | |
| 41 | 803.673671 | 91 | 806.683256 | 141 | 816.099241 | 191 | 832.597948 | 241 | 747.232163 | | |
| 42 | 759.59015 | 92 | 802.147202 | 142 | 789.968935 | 192 | 819.602826 | 242 | 810.233363 | | |
| 43 | 702.058027 | 93 | 804.07556 | 143 | 744.800287 | 193 | 812.660474 | 243 | 827.391614 | | |
| 44 | 700.234976 | 94 | 785.645205 | 144 | 725.433882 | 194 | 799.247801 | 244 | 832.532566 | | |
| 45 | 710.800476 | 95 | 802.418781 | 145 | 761.26038 | 195 | 762.818368 | 245 | 822.984174 | | |
| 46 | 738.464654 | 96 | 805.925579 | 146 | 776.030182 | 196 | 764.208878 | 246 | 822.086506 | | |
| 47 | 800.322372 | 97 | 808.996178 | 147 | 783.801378 | 197 | 742.373531 | 247 | 779.739309 | | |
| 48 | 848.024535 | 98 | 797.584311 | 148 | 780.906733 | 198 | 737.761919 | 248 | 759.077036 | | |
| 49 | 864.207466 | 99 | 816.220023 | 149 | 766.721753 | 199 | 737.649349 | 249 | 768.618503 | | |
| 50 | 855.137659 | 100 | 820.860871 | 150 | 714.005018 | 200 | 734.326689 | 250 | 760.742503 | | |

SYSTEM AND METHOD FOR RELAXATION

TECHNICAL FIELD

The invention concerns a system and method for relaxation.

BACKGROUND OF THE INVENTION

Heart rate variability (HRV) is a predictive indicator of survival after a heart attack. Over half a dozen prospective studies have shown that reduced HRV predicts sudden death in patients with MI, independent of other prognostic indicators such as ejection fraction. HRV refers to the extent of heart rate fluctuation and reflects the modulation of cardiac function by the autonomic nervous system and other physiological regulation systems. HRV analysis is a recognized tool for the estimation of cardiac autonomic modulation. More HRV means your heart is better able to adapt to changing circumstances. Less HRV means nerves and heart muscle cannot respond easily to change, potentially leading to out-of-rhythm beats or an abrupt, fatal stop. Less HRV appears to be a marker of fatal ventricular arrhythmia.

Stress may reduce HRV by affecting nerves that control the heart: The heart can be soothed and protected by stress reduction and exercise. Preliminary evidence suggests that both improve HRV. People can suffer from stress at work, at college, at home and virtually anywhere at anytime. It is well documented that stress not only affects one's immediate emotional state and mood, but also bodily functions in general. Stress and the stress hormone upset the autonomic systems of our body and endanger our health, in particular the health of our brain. Heart rate has been found to be a good indicator and quick signal of stress. The severity of stress can be expressed through changes in heart rate variability. This can damage brain cells, which will become more vulnerable to neurological insult, leading to brain ageing, stroke, and possibly Alzheimer's disease. There is a pressing need for strategies to reduce stress.

Baroreceptors situated in the aorta and internal carotid arteries play an important role in maintaining normal cardiovascular function and blood pressure. These receptors help to regulate our bodily functions by modulating cardiac function via autonomic and other physiological regulation systems. The rate and intensity of pressure signals at these receptors respond to our cardiac needs as a reaction to stressors experienced by the body. This response is exhibited in the form of blood pressure, heart rate changes and arousal of emotions. As bio-signals, such responses can be measured by changes in the is heart beat which are precisely represented by HRV using spectrum analysis.

Stress is different from anxiety due to the presence of an identifiable cause. Anxiety is a normal reaction to stress. However, the symptoms of anxiety and stress are driven by the same chemical reaction, with the same symptoms of a higher heart rate, sweaty palms and churning stomach. All these symptoms, and others, are explained by the physiological changes that occur when the mind and body experience stress or anxiety. The terms 'anxiety' and 'stress' are used interchangeably in the present application.

SUMMARY OF THE INVENTION

In a first preferred aspect, there is provided a method for relaxation, the method comprising:

processing the electrocardiogram (ECG) of a user to remove noise and analyse the ECG signal in the time and frequency domains;

computing an index of stress from the processed ECG; and providing real-time biofeedback by communicating the index of stress to the user together with a relaxation video to cause the user to relax.

The real-time biofeedback may be any one from the group consisting of: a visual display of the index of stress, an audio response about the index of stress, a tactile-based response corresponding to the index of stress, and a combination thereof.

The index of stress may be computed by extracting the heart rate and power spectral density of low frequency (LF) and high frequency (HF) from the processed ECG.

The index of stress may be computed by:

determining the distance from the co-ordinate of (LF, HF) to the centre of an autonomic balance diagram; and dividing the distance by 5.65 and multiplying by 10;

wherein if the distance is greater than 5.65, the index of stress is set to 10.

The index of stress may be represented by a horizontal color chart.

The method further comprising communicating the ECG signal, Heart Rate Variability (HRV) and relaxation instructions to the user.

Communicating may include displaying the index of stress, ECG, HRV and instructions to the user via goggles worn by the user.

In a second aspect, there is provided a system for relaxation, the system comprising:

electrodes worn by a user to measure the electrocardiogram (ECG) of the user;

a processor to process the ECG to remove noise and analyse the ECG signal in the time and frequency domains, and compute an index of stress from the processed ECG; and a multimedia device to provide real-time biofeedback by communicating the index of stress to the user together with a relaxation video to cause the user to relax.

The multimedia device may be any one from the group consisting of: goggles to be worn by the user, LCD screen, ear phones, loudspeakers and a combination thereof.

In a third aspect, there is provided a method for generating an index of stress having a range from 1 to 10, the index of stress being communicated to relax a user, the method comprising:

determining the distance from a co-ordinate of (LF, HF) of a processed ECG to the centre of an autonomic balance diagram; and dividing the distance by 5.65 and multiplying by 10;

wherein if the distance is greater than 5.65, the index of stress is set to 10.

The index of stress may be communicated to the user graphically, in audio form or in tactile response.

In human beings, anxiety is accompanied by changes in the autonomic nervous system function, including increased heart rate, body temperature and blood pressure, and decreased heart rate variability. Studies suggest that anxiety may be a possible cause of autonomic nervous system dysregulation in cardiac events and sudden death. The low- to high-frequency HRV ratio (LF/HF ratio) at rest was higher in people with higher anxiety levels. This results in sympathovagal imbalance and sympathetic hyperactivity, thereby increasing the risk for ventricular fibrillation. There was a positive correlation between trait anxiety and LF/HF ratio.

The present invention uses the Heart Rate Variability (HRV) index to develop a pervasive and interactive Audio-Visual (AV) system for relaxation. This immediate application of the present invention is for stress management. It measures the stress of the user and displays the results to provide real time biofeedback. The system also instructs the user on the best way to relax according to his/her present condition.

The system may become a main component of an integrative health monitoring system and telehealth kiosks. The functions of the stand-alone device maybe further enhanced for long-time health monitoring. When a critical illness occurs, the device will alert the patient to ask for prompt medical treatment.

BRIEF DESCRIPTION OF THE DRAWINGS

An example of the invention will now be described with reference to the accompanying drawings, in which:

FIG. 10 is a table of data of RR Intervals

DETAILED DESCRIPTION OF THE DRAWINGS

Figure 1:
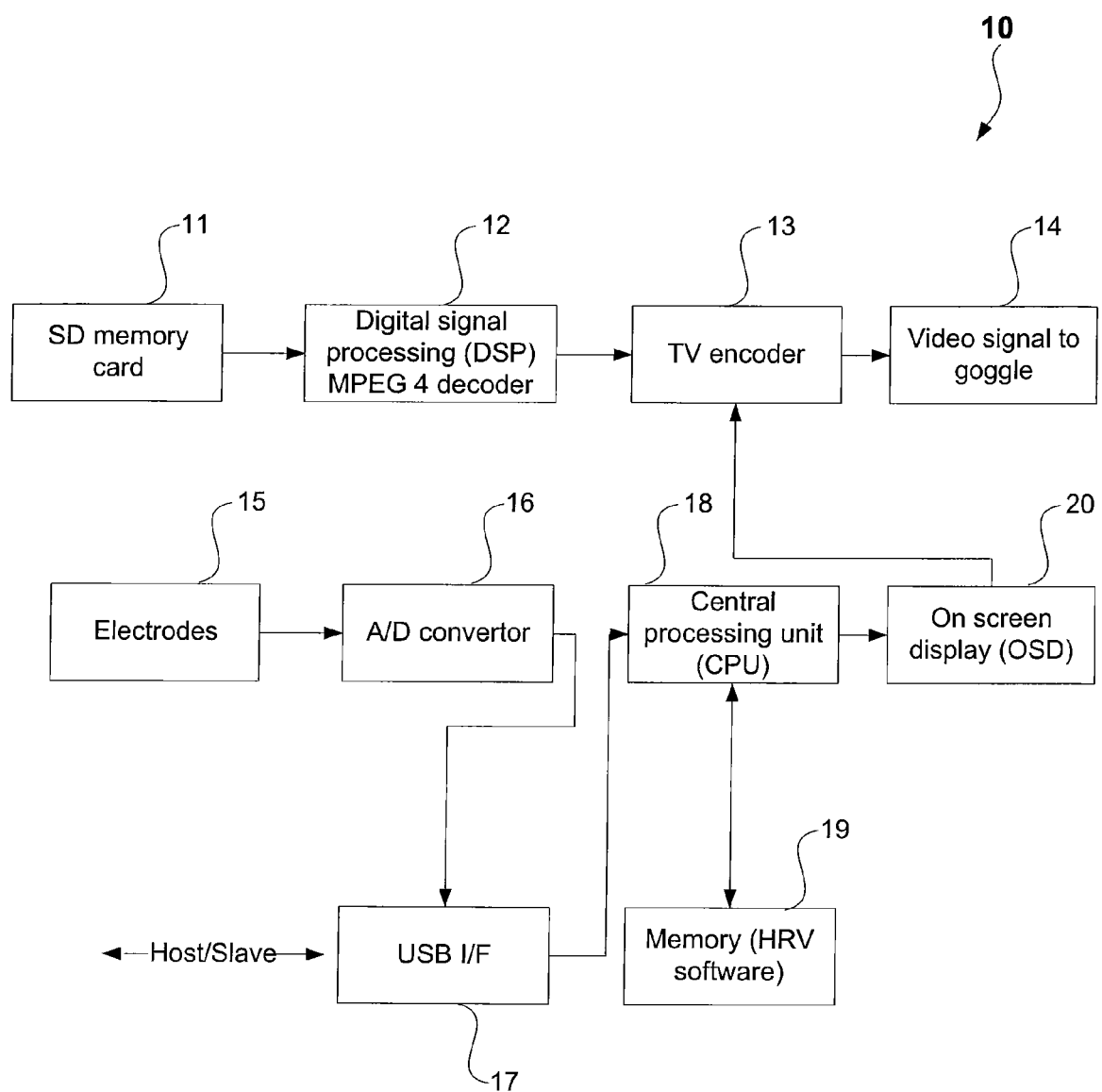
FIG. 1 is a block diagram of a system in accordance with a preferred embodiment of the present invention depicting the link between hardware and software components.

Referring to FIG. 1, Heart Rate Variability (HRV) is measured to determine the stress level of a user and is used to relax the user. In the system, hardware measures the electrocardiogram ECG of the user through the skin contact of electrodes 15 on wrists or ears. The measured ECG is processed by a processor 18 via an input/output interface. The raw ECG signal is processed to remove the noise and is then analysed in the time and frequency domains. A time domain measure is the calculation of the standard deviation of beat-to-beat intervals. Frequency domain method is the application of the discrete Fourier transform to the beat-to-beat interval time series. The heart rate and power spectral density of the low frequency and high frequency are extracted and the index of stress is calculated and saved.

Referring to FIG. 1, the analog to digital (A/D) convertor 16 and the electrodes 15 are the hardware used to measure the ECG of the user. The electrodes 15 are connected to the left and right wrist and the leg of the user. The A/D convertor 16 consists of a very high precision and low noise instrumentation amplifier and an analog to digital convertor. The ECG signal from the user is captured through the electrodes 15, amplified by the instrumentation amplifier and the signal is converted to a digital number by the A/D convertor 16. The raw ECG signal is processed and analysed using a processor 18 which receives the digitized signal from the A/D convertor 16. The application software is stored in a memory 19. The memory 19 also stores a database for the results for multiple users and multiple measurement sessions. The database manages the HRV results of many users at different times. Usage of the memory 19 can be shared by a group of people until it is full. In real-time, the HRV results are mixed with the output of the MPEG 4 decoder 12 (or any media player) through the TV encoder 13 and projected on a pair of LCD goggles 14 for the user to see. Mixing may include overlaying or presenting both the HRV results and the output of the MPEG 4 decoder 12 adjacent to each other.

The HRV results and time recordings may also be stored in the flash memory 11 and transferred to the PC for a complete detailed analysis. Alternatively, the results may be sent to a healthcare professional for consultation and expert advice. The progress of relaxation in a period can be saved and reviewed.

The processor 18 has a built in program and memory 19 for software to perform signal processing including the noise reduction, ECG parameters extraction, time domain and frequency domain analysis. The heart rate and power spectral density of low frequency (LF) 51 and high frequency (HF) 52 from the processed ECG is used to calculate the Heart Rate Variability (HRV) and the index of stress. The device for the system 10 may be a stand-alone dedicated hardware unit, a personal digital assistant (PDA) or a personal computer (PC). The device indicates the user's stress level and teaches him/her how to relax. The results of the HRV and index of stress are displayed via the On Screen Display (OSD) 20. When the CPU is a stand-alone hardware, the OSD 20 can be a signal only which is combined with the video signal in the TV encoder 13 and displayed onto the goggles. When the processor 18 is provided on a PDA, the OSD 20 can be the LCD screen of the PDA or a signal to the goggles 14. When the processor 18 is provided in a PC, the OSD 20 may be a monitor or a signal to the goggles 14.

The SD Card 11, Digital Signal Processing (DSP) unit (MPEG 4 Decoder) 12, the TV encoder 13 and the goggles 14 provide a pervasive audio/video system 10. The hardware and software can be integrated into a single portable device with LEDs, LCD and a speaker or earphone. This device can be connected to a portable audio/video media player or to an integrative diagnosis system. This system 10 may be provided as a stand-alone system, a built-in system on a PDA or a personal computer (PC), or embedded into other devices, for example, a portable AV system. The benefit is that the user can relax himself with his favourite activity, for example, yoga, watching movies. So instead of a predetermined relaxation video, alternative multimedia content may be presented. If this system is a built-in system on a PDA or a PC, it can be a software decoder of MPEG 4 video. The TV encoder 13 combines the video signal and the HRV displayed results and projects them onto the goggles 14. If the audio/video system 10 is a built-in system on a PDA or a PC, the TV encoder 13 is part of the OSD 20 and the goggles 14 are connected to the OSD 20 directly. If the entire system 10 is integrated into a Personal Digital Assistant (PDA), the A/D convertor 16 is connected to the PDA via a USB interface (USB I/F) 17. The software is executed on the PDA and the results are displayed on the screen of the PDA. The results are stored in a memory 19 of the PDA.

The display format of the index of stress may be provided via an LED screen, text, graphics, colour bar 33, on an LCD computer screen, or a pair of LCD goggles 14, or sound and voice through a speaker or earphones. Real-time biofeedback is not limited to an on-screen display and LED indicators. Audio and voice instructions are very helpful for those suffering from visual impairment. The voice or sound is also better heard by those suffering from conductive deafness.

Preferably, the portable device of the system 10 is light and portable. The user can bring it on long journeys or use it for long-term body health monitoring. The latter is very useful for some critical illnesses, for example, apoplexy, which require prompt medical treatment. It is also very useful for problems such as sleep apnea, insomnia, which require long-term treatment. The device may be merged to an integrative diagnosis system with other instruments, for example, blood pressure monitor, pulse oximeter to provide a complete biological diagnosis of the user. The functions of the device can be enhanced in the future through firmware and software upgrades.

Figure 2:
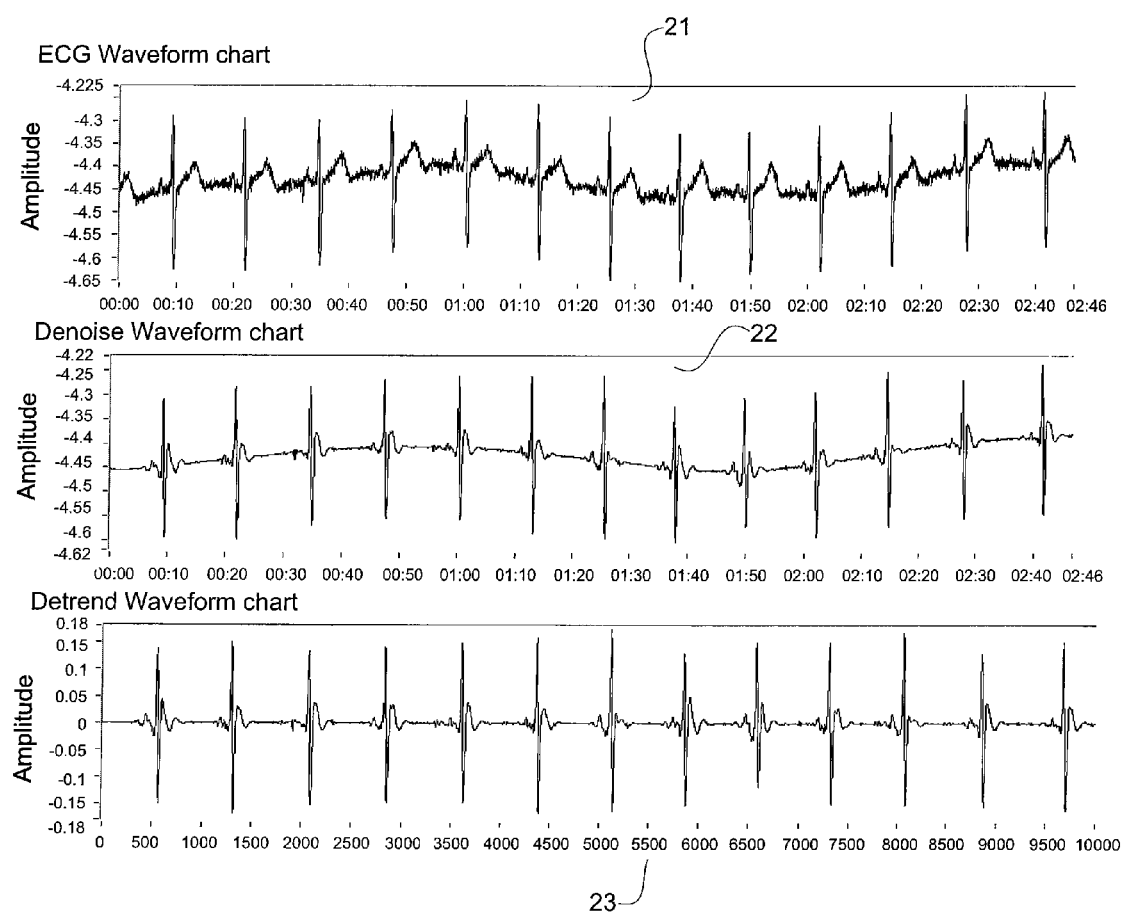
FIG. 2 is a graphical depiction of raw and processed ECG signals of the system of FIG. 1.
Figure 3:
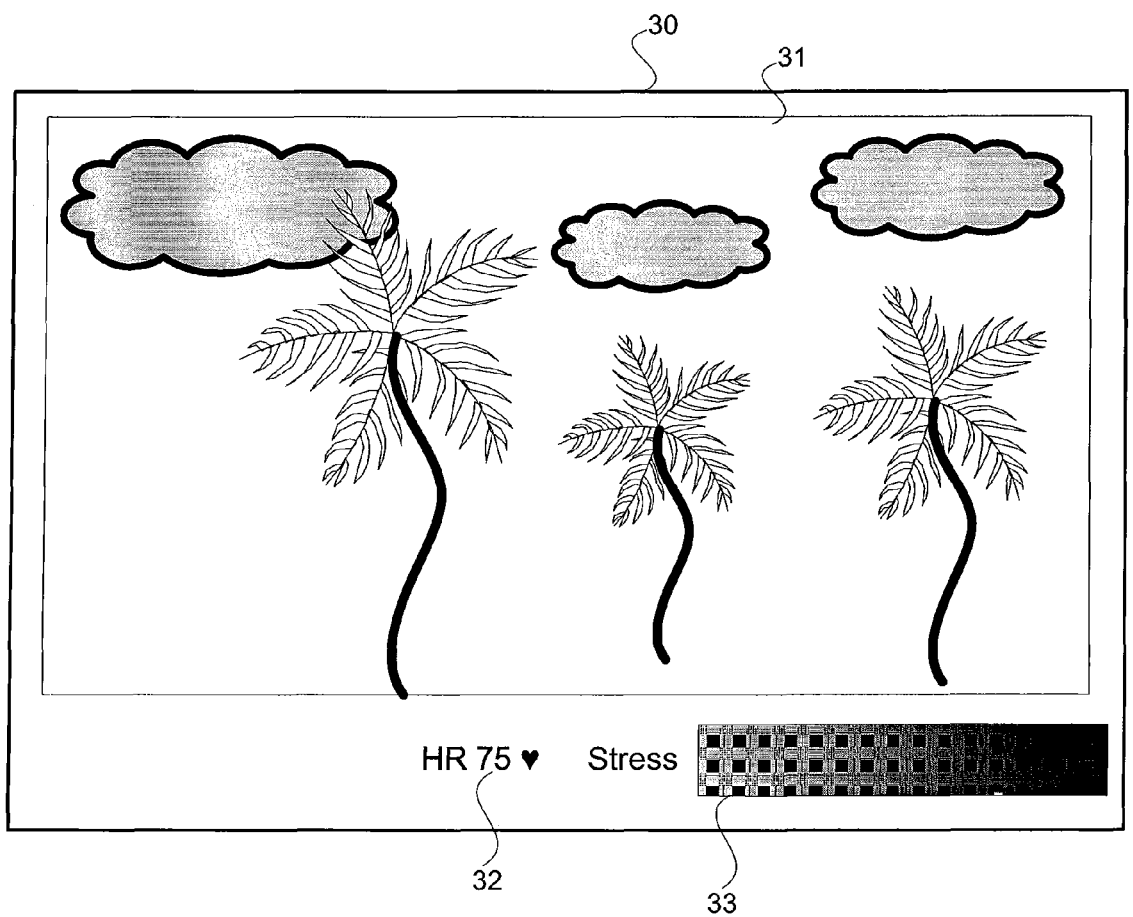
FIG. 3 is a screenshot of the video displayed to the user generated by the system of FIG. 1.

Referring to FIG. 2, three diagrams are illustrated from top to bottom: the raw ECG signal, a denoise waveform chart of the ECG signal and the detrend waveform graph of the ECG signal. The advantage of using two dimensional graphs to represent the heart rate is that it is easily understood by the user. However, in some embodiments, a 2D diagram is not suitable for display while the relaxation video is playing because the 2D diagram occupies too much area on the screen 30. Instead of displaying the 2D diagram, a rainbow coloured bar 33 is displayed as depicted in FIG. 3. The rainbow bar 33 is converted from the original 2D diagram. The rainbow bar 33 does not occupy too much area on the screen 30 so that it can be displayed below a relaxation video. Display of the rainbow bar 33 provides a real time bio-feedback to the user so they can learn how to relax from observing real-time changes to the rainbow bar 33.

Referring to FIG. 3, the screen 30 of the user's goggles 14 displays the heart rate 32 and index of stress 33 in real time. A relaxation video 31 is also displayed to relax the user. The relaxation video 31 may be of a beach, waterfall or some other type of soothing scenery. Other items that may be displayed include the ECG, the HRV, and instructions to the user to relax (breathing technique, etc). After a HRV measurement session is completed, the user can review the statistics and a summary of the session is provided. The results can also be displayed on a desktop computer to a physician or healthcare worker.

Biofeedback is a technique for receiving some form of auditory, visual or tactile signal indicating changes in a biological process. It operates on an input-process-output model. Input refers to the incoming auditory or visual signal, process is the interpretation of the received signal, and output refers to the changes in the biological state as a result of this process. The system 10 operates on the principle of biofeedback which works on an input-process-output model. It allows the users to be aware of their stress cognitively and then alters their responses by performing some kinds of relaxation exercise, for example, breathing. The input signal, stress state is shown on the rainbow bar 33 in different colours to indicate the 0 to 10 stress level. The rainbow bar 33 is visualized through the goggles 14. By observing the changes to the rainbow bar 33, users learn how to relax chronically tensed muscles or chronically aroused autonomic functions through breathing exercises. Stress is relieved because it is usually more tolerable in a state of relaxation. Relaxation techniques are prompted and are used to overcome anxiety which raises the threshold easier and readily with the visualization of stress level.

Figure 4:
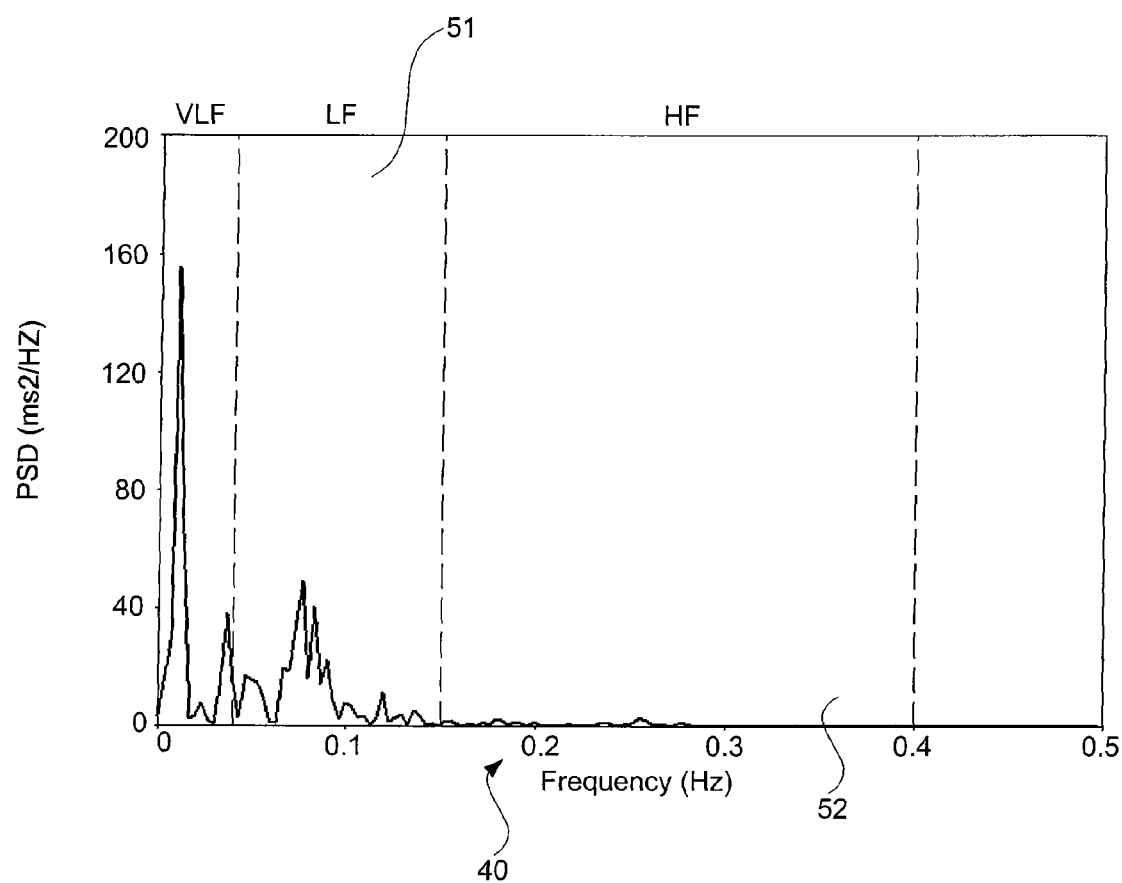
FIG. 4 is a power spectral density diagram of the processed ECG signal of FIG. 2.

Referring to FIG. 4, the power spectral density is plotted on the diagram which calculates the LF 51 and HF 52. An analysis of HRV in the frequency domain is obtained using LF 51 and HF 52. The statistics of the heart rate and the changes of heart rate are the analyses of HRV in time domain. The natural logarithms of the areas under the curve in LF 51 and HF 52 of the processed ECG signal 40 are computed. A point (LF, HF) 53 is located on a 2D plane as illustrated by the solid dot of FIG. 5. LF is 6.64 and HF is 5.5585. This represents the user's heart characteristics in real-time. The stress level is defined as the distance from the point (LF, HF) 53 to the centre 55 of a rectangle 54 representing a preferable low stress level. The enclosed area of the rectangle 54 represents the optimum area of the autonomic balance. It is desirable for user to relax such that the point 53 falls within this rectangle 54. The (x, y) co-ordinates of the centre 55 of the rectangle are (6.94, 5.65). The equation to calculate the stress level is the distance from (LF, HF) to the centre+5.65×10. If the distance is greater than 5.65, then the stress level is set to 10.

Figure 6:
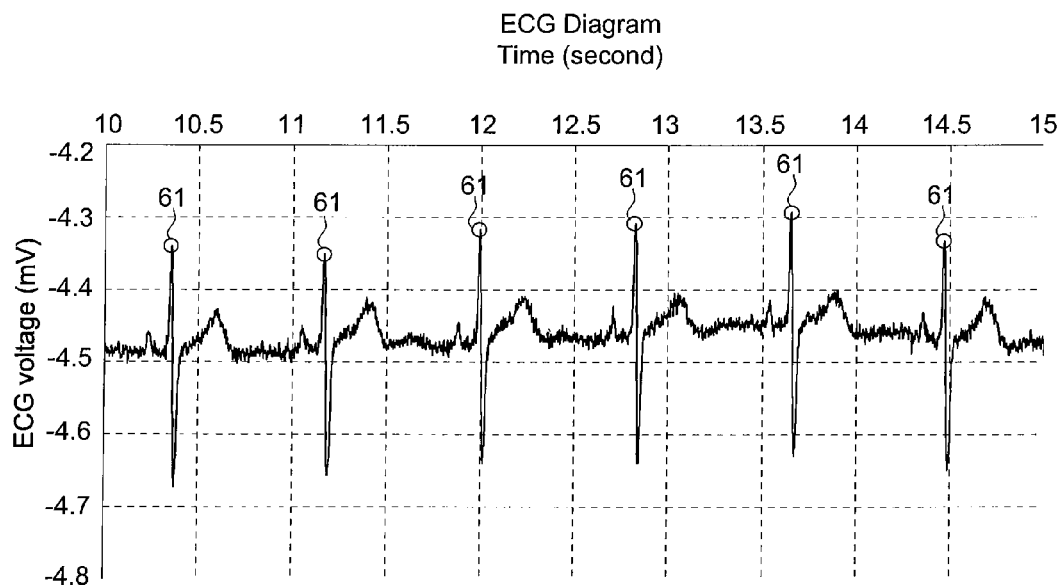
FIG. 6 is an ECG Diagram.

Referring to FIG. 6, the ECG signal is captured using the electrodes 15 and a high precision instrumentation operational amplifier. The raw analog ECG signal that is captured is then converted to digital form using the analog-to-digital converter (ADC) 16. Each digital sample is 14-bit and the sampling frequency is 1000 Hz. For an ECG recording of five minutes, there are 300,000 samples. After the raw ECG is digitized, signal processing techniques are applied to locate all the R peaks 61. The located R peaks 61 are circled in FIG. 6.

After the R peaks 61 are located, the period of each heart beat is calculated. The period is the time distance between the previous R peak and the current R peak. For calculation of HRV, a recording of ECG for a few minutes at least is required. The second located R peak is used as a reference starting point and the time at this moment is set to zero. In the RR Interval Diagram depicted in FIG. 7, the x-axis is the time (relative to the reference starting point) of the R peaks and the y-axis is the period of heart beat in seconds. The original RR interval curve 71 is the line above in FIG. 7. The x value of the first point is 0 and the y value is the time difference between the first R peak and the second R peak. The x value of the second point is the x value of the first point plus the y value of the first point. The y value of the second point is the time difference between the second R peak and the third R peak. In general, the x value of the $n^{th}$ point is the x value of the $(n-1)^{th}$ point plus the y value of the $(n-1)^{th}$ point. The y value of the $n^{th}$ point is the time difference between the $n^{th}$ R peak and the $(n+1)^{th}$ R peak. The data of RR Interval is listed in the table of FIG. 10.

Figure 8:
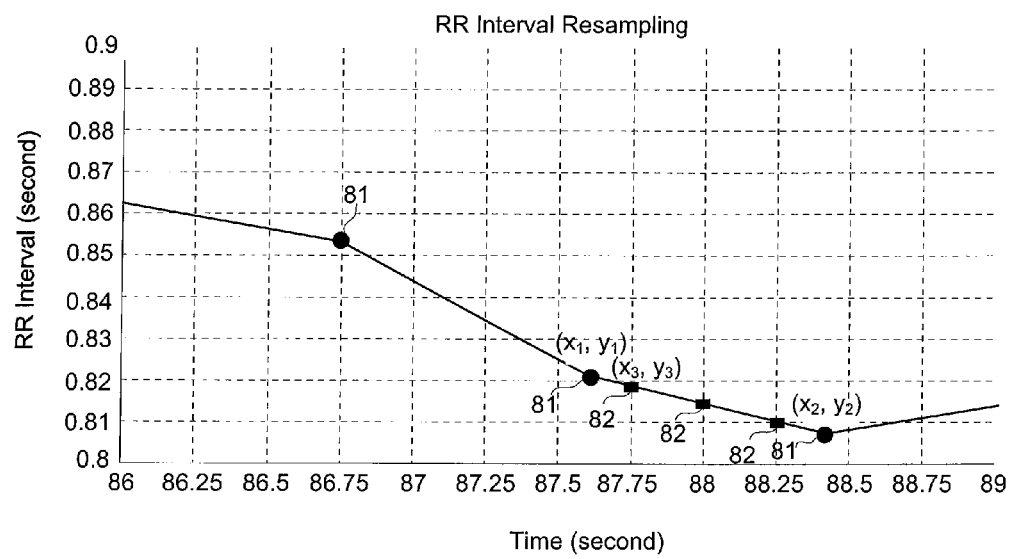
FIG. 8 is a resampling of the RR Interval Curve.

After the RR Interval Diagram is plotted, the original RR Interval Curve 71 is resampled for Fast Fourier Transformation for the frequency spectral analysis. The RR Interval Curve is treated as a continuous function against time. It is assumed that the heart rate is less then 2 Hz (120 beats per minute). According to Nyquist-Shannon sampling theorem, the sampling frequency needs to be at least double of the highest frequency component (2 Hz in this example). Therefore the sampling frequency is set to 4 Hz. This means a sample is required every 0.25 second. The sampling points do not align with the R peaks 61. The number of these sampling points is a few times more than the number of R peaks. An interpolation technique is applied to locate the extra sampling points on the original RR Interval Curve 71. In FIG. 8 the circular dots 81 are the points on the original RR Interval Curve 71. The square points 82 are interpolated points. For example, $(x_3, y_3)$ is found between $(x_1, y_1)$ and $(x_2, y_2)$, $x_3$ is 87.75 (aligned with the sampling time) and $y_3$ is calculated using the two-point form:

$$\frac{(y_3 - y_1)}{(x_3 - x_1)} = \frac{(y_2 - y_1)}{(x_2 - x_1)} \qquad \text{Equation 1}$$

-continued $$y_3 = (x_3 - x_1)\frac{(y_2 - y_1)}{(x_2 - x_1)} + y_1 \qquad \text{Equation 2}$$

Figure 7:
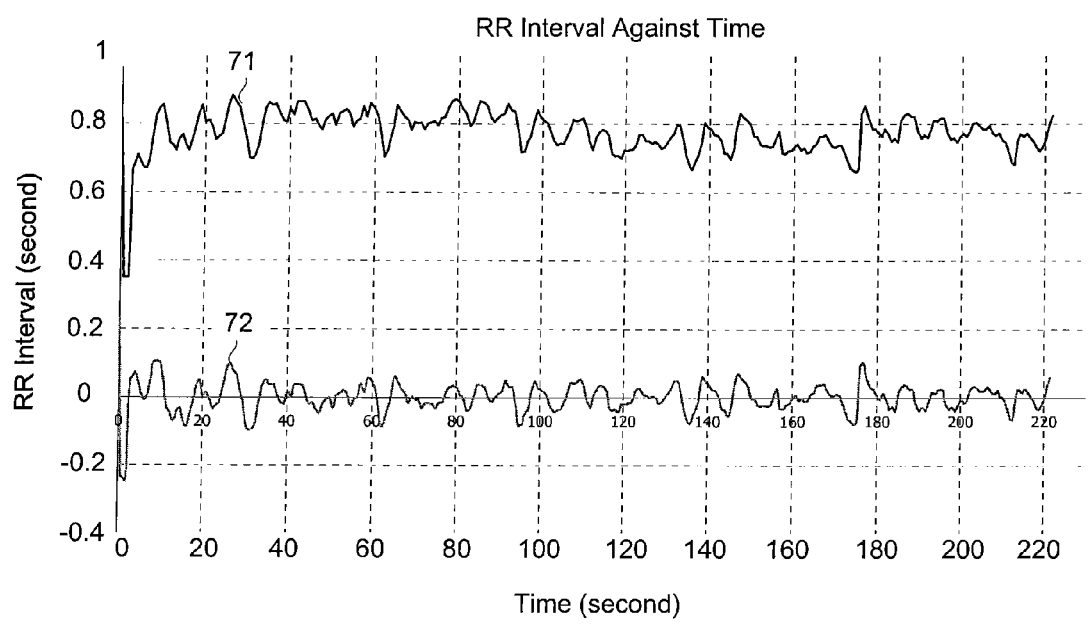
FIG. 7 is an original RR Interval Curve and a relocated and resampled RR Interval Curve.

After the resampling of the RR Interval Curve 71, signal processing techniques are applied to remove the offset of the resampled RR Interval Curve. This process is similar to signal processing for an electrical signal. The direct current (DC) component is removed and only the alternative current (AC) components are retained. The relocated and resampled RR Interval Curve 72 is shown in FIG. 7. The shape of this curve 72 is basically the same as the original RR Interval Curve 71 but with more points.

A Fast Fourier Transformation is applied for the relocated and resampled RR Interval Curve 72 using the following equation:

$$F(2k) = \sum_{n=0}^{\frac{1}{2}N-1} \left[x(n) + x\left(\frac{1}{2}N + n\right)\right](W^2)^{nk} \qquad \text{Equation 3}$$

$$F(2k+1) = \sum_{n=0}^{\frac{1}{2}N-1} \left[x(n) - x\left(\frac{1}{2}N + n\right)\right]W^n(W^2)^{nk} \qquad \text{Equation 4}$$

where $$k = \left(0, 1, 2, \ldots, \frac{1}{2}N - 1\right),$$

N is the total number of sampling points and $$W = e^{\frac{-j2\pi}{N}} \qquad \text{Equation 5}$$

Figure 9:
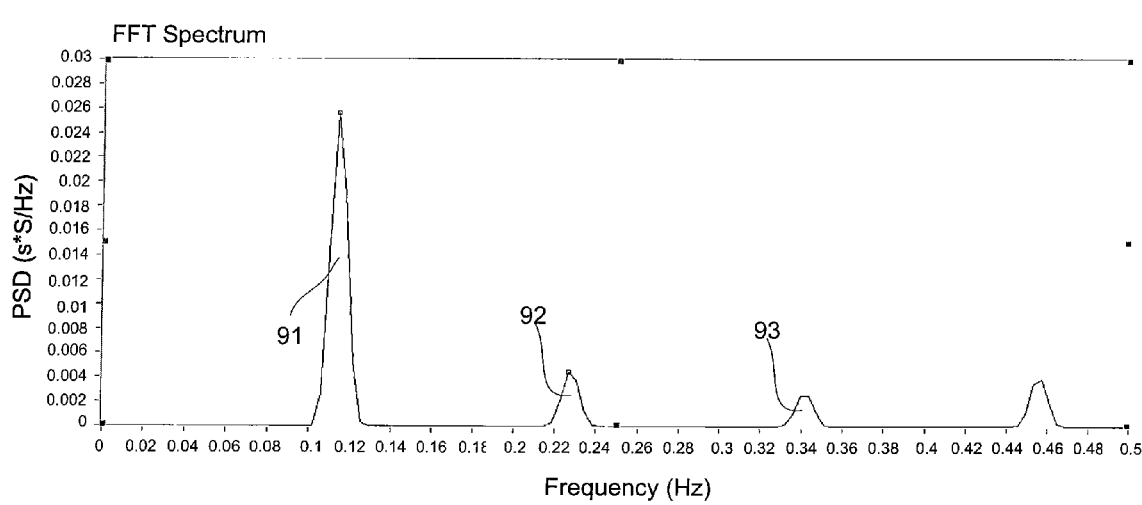
FIG. 9 is a Power Spectral Density diagram.

After the calculation, a Power Spectral Density is obtained as shown in FIG. 9.

Figure 5:
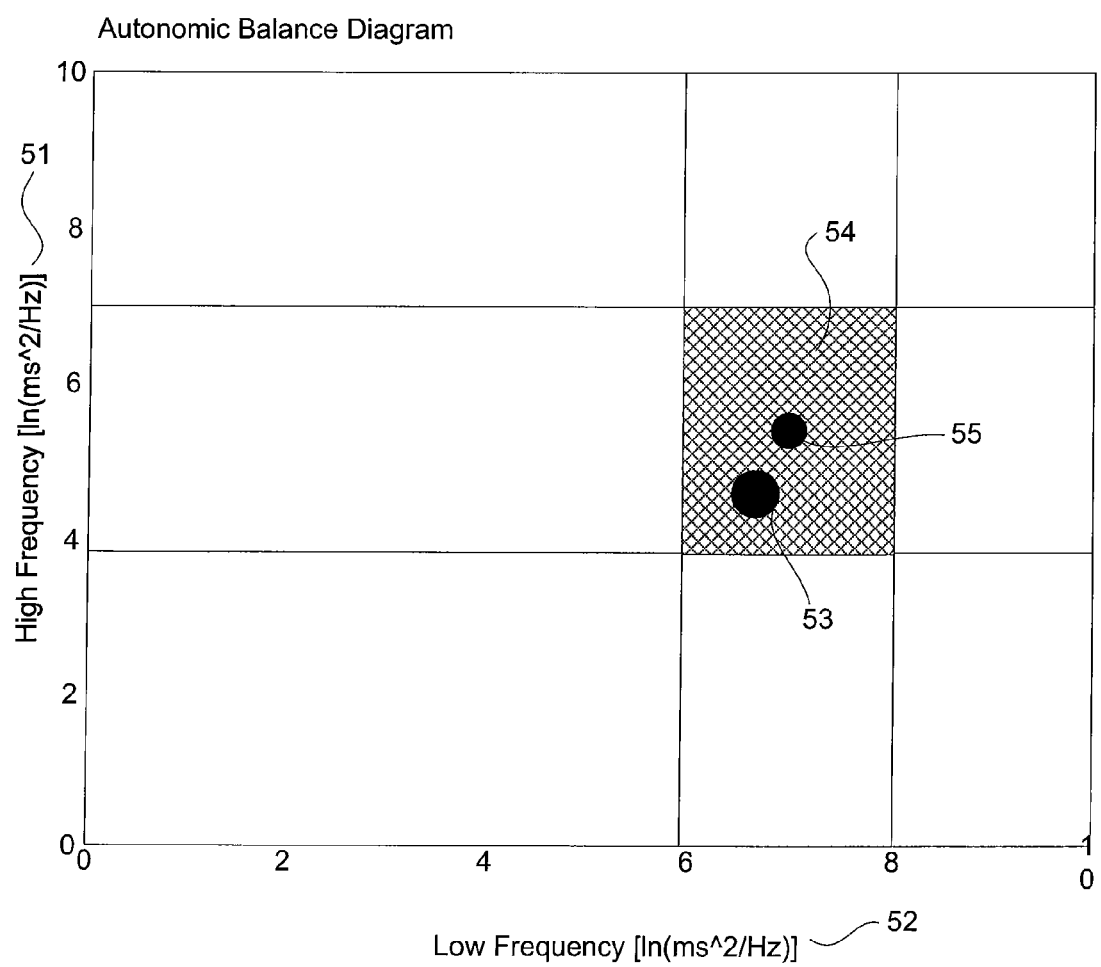
FIG. 5 is an autonomic balance diagram of the processed ECG signal of FIG. 2.

The LF is natural logarithm of the total area 91 under the Power Spectral Density Curve for the frequency from 0.04 Hz to 0.15 Hz. The HF is natural logarithm of the total area 92 under the Power Spectral Density Curve for the frequency from 0.15 Hz to 0.4 Hz. In the described example, the LF and HF are 6.64 and 5.55851 respectively. In FIG. 5, the bigger dot 53 is the calculated (LF, HF). The smaller dot 55 is a reference optimum point which represents the state of no stress.

The Stress Level is calculated based on the ratio of the distance between the point (LF, HF) to the reference optimum point to 5.65. The distance between (LF, HF) to the reference point is calculated as:

$$d = \sqrt{(6.94 - LH)^2 + (5.65 - HF)^2} \qquad \text{Equation 6}$$

The Stress Level is calculated as:

$$\text{Stress Level} = \frac{d \times 10}{5.65} \qquad \text{Equation 7}$$

which is 0.56 in the described example. If the Stress Level is greater than 10, then it is set to 10.

The system 10 integrates real time biofeedback with a relaxation video 31. The concept of real time bio-feedback is not limited to visual display. It can be a real time bio-feedback in any form, for example, sound, touch. With this bio-feedback, the user may be able to learn how to relax with minimal training. The learning effectiveness and efficiency are highly improved because the user is aware of the current level of stress and the immediate effect of his/her responses and relaxation techniques.

With proper training in the use of and reaction to the input signals, HRV may be used as a training signal to recognize the biofeedback prompt (input) as a catalyst for the user to start their relaxation exercises.

It is envisaged that elements of immersion are included to increase the effectiveness of relaxation, thus relieving the symptoms. Immersion can be created by engaging the user visually and audibly using the monitoring parameter, HRV, as a training signal. This postulation is grounded on studies in the elderly with wound and burn injuries.

The physical size of the device may be further minimized so that it can be embedded in audio-visual (AV) systems in the market. Different versions of the same product will be developed for different platforms (PC, PDA, portable AV system, integrative health monitoring system.) Additional software functions are envisaged to enhance the accuracy and reliability. It is envisaged that the device can be used in the diagnosis of other illnesses.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

What is claimed:

1. A method for relaxation, the method comprising:
   processing, using a processor, an electrocardiogram (ECG) of a user to remove noise and analyse the ECG signal in the time and frequency domains;
   computing an index of stress from the ECG signal processed; and
   providing real-time biofeedback by communicating the index of stress to the user together with a relaxation video to cause the user to relax,
   wherein the real-time biofeedback is any one from the group consisting of: a visual display of the index of stress, an audio response about the index of stress, a tactile-based response corresponding to the index of stress, and a combination thereof, and
   wherein the index of stress is computed by:
   determining the distance from the co-ordinate of (LF, HF) to the centre co-ordinates of an area representing an optimum area of autonomic balance on an autonomic balance two-dimensional diagram; and
   dividing the distance by 5.65 and multiplying by 10;
   wherein if the distance is greater than 5.65, the index of stress is set to 10 and wherein the value 5.65 represents HF at optimum preferred stress level at rest and the index of stress of 10 represents the maximum upper limit of stress.

2. The method according to claim 1, wherein the index of stress is computed by extracting the heart rate and power spectral density of low frequency (LF) and high frequency (HF) from the ECG signal processed.

3. The method according to claim 1, wherein the index of stress is represented by a horizontal color chart.

4. The method according to claim 1, further comprising communicating the ECG signal, Heart Rate Variability (HRV) and relaxation instructions to the user.

5. The method according to claim 4, wherein communicating includes displaying the index of stress, ECG, HRV and instructions to the user via goggles worn by the user.

6. A method for generating an index of stress having a range from 1 to 10, the index of stress being communicated to relax a user, the method comprising:
   determining, using a processor, the distance from a co-ordinate of (LF, HF) of a processed ECG to the centre co-ordinates of an area representing an optimum area of autonomic balance on an autonomic balance two dimensional diagram; and
   dividing the distance by 5.65 and multiplying by 10;
   wherein if the distance is greater than 5.65, the index of stress is set to 10, wherein the value 5.65 represents HF at optimum preferred stress level at rest and the index of stress of 10 represents the maximum upper limit of stress.

7. The method according to claim 6, wherein the index of stress is communicated to the user graphically, in audio form or in tactile response.

8. The method according to claim 7, wherein the index of stress is represented by a horizontal color chart.

* * * * *